United States Patent [19]

Ronchi

[11] 4,307,030

[45] Dec. 22, 1981

[54] PROCESS AND APPARATUS FOR PRODUCING SUBSTITUTED THIOCARBAMATES

[75] Inventor: Nello Ronchi, Pinzano, Limbiate, Italy

[73] Assignee: Oxon Italia S.p.A., Milan, Italy

[21] Appl. No.: 966,632

[22] Filed: Dec. 5, 1978

[51] Int. Cl.$^3$ .................. C07C 155/03; B01J 8/02
[52] U.S. Cl. .................. 260/455 A; 422/235; 422/234; 422/225; 422/211; 422/189
[58] Field of Search .................. 260/455 A; 422/235, 422/234, 225, 189, 211

[56] References Cited

U.S. PATENT DOCUMENTS 3,151,119  9/1964  Grisley et al. .................. 260/455 A Primary Examiner—John M. Ford
Assistant Examiner—Robert C. Whittenbaugh
Attorney, Agent, or Firm—Stevens, Davis, Miller & Mosher

[57] ABSTRACT

Substituted thiocarbamates are produced by continuously feeding together a secondary amine and sulphur in stoichiometric proportions and in a suitable solvent into a reaction column subjected to pressure by carbon monoxide. A continuous circulation of the reaction solution is maintained in the column, and the effluent is subjected to alkylation, the substituted carbamate being derived therefrom continuously.

5 Claims, 1 Drawing Figure

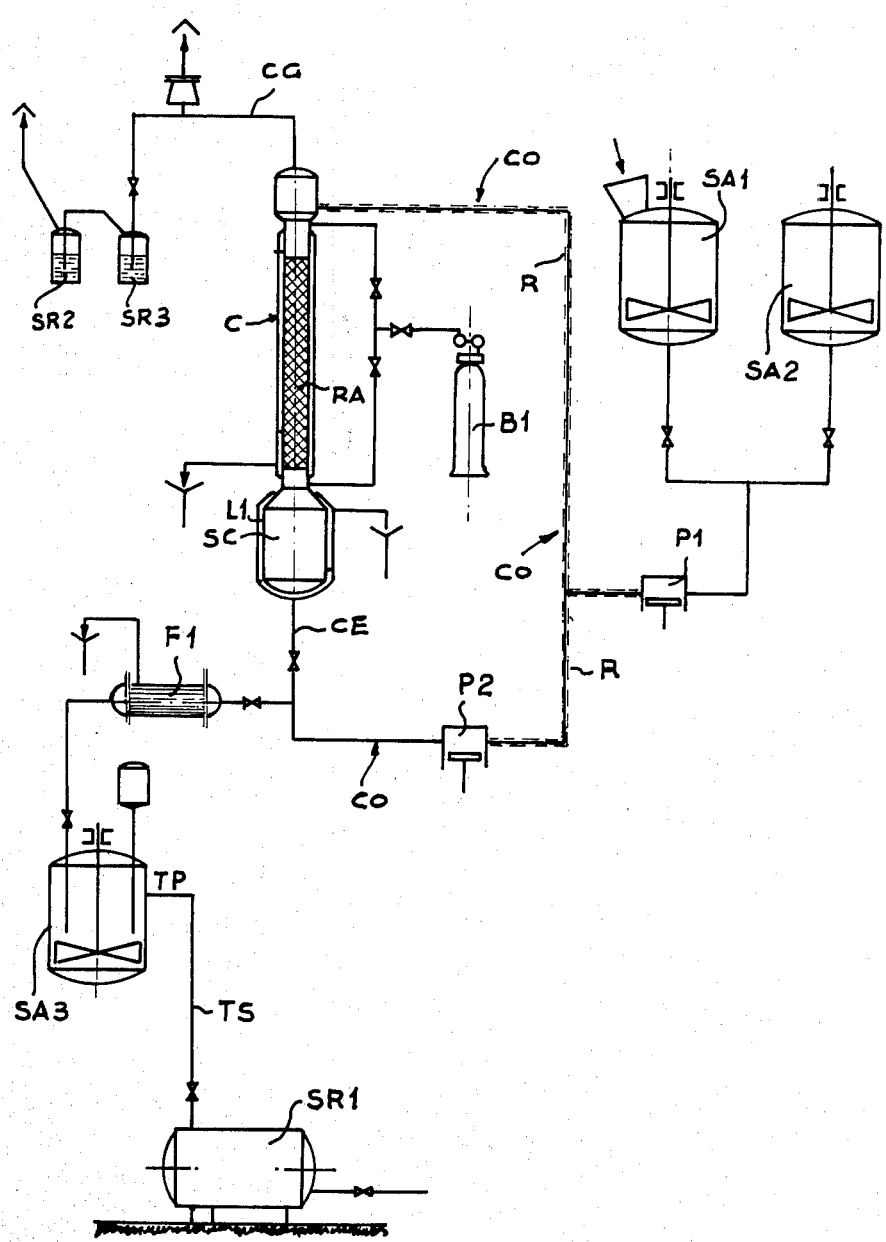

PROCESS AND APPARATUS FOR PRODUCING SUBSTITUTED THIOCARBAMATES

BACKGROUND OF THE INVENTION

The present invention relates to a process for producing substituted thiocarbamates in a continuous cycle.

It is known from the literature that it is possible to synthesize thiocarbamates by reacting a secondary amine with carbon monoxide and sulphur in a suitable solvent and thereafter subjecting the product obtained to alkylation.

The reactions are as follows:

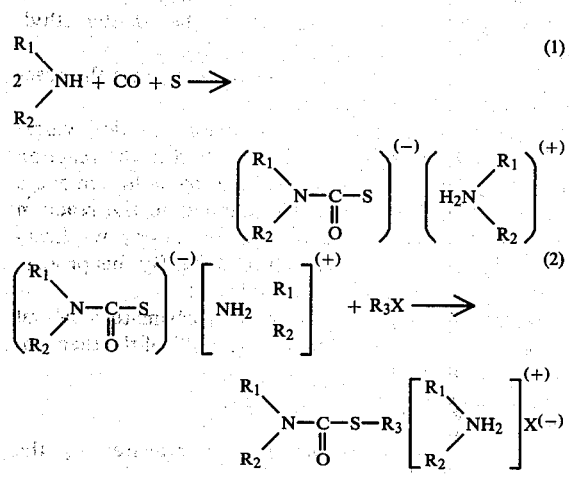

wherein:
  $R_1$, $R_2$ may be the same or different, consisting of alkyl, cycloaklyl or aralkyl radicals, or may form together a bivalent polymethylene radical.
  $R_3$ = an alkyl, cycloalkyl or aralkyl radical.
  X = a substituted group consisting of halide, sulphate or sulphonate.

In essence, it happens that in reaction (1) the secondary amine reacts with the carbon monoxide and sulphur to give rise to a substituted ammonium salt of thiocarbamic acid, after which in reaction (2) this salt reacts with an alkylating agent, forming the substituted thiocarbamate.

Deep study of the mechanism by which the aforesaid known reactions occur and a long series of experiments have now enabled the Applicants to develop an improved process and apparatus for producing substituted thiocarbamates.

In effect, heretofore the first of the above-mentioned reactions has always been conducted in the presence of an excess of sulphur by mixing equal molar amounts of secondary amine and sulphur in the presence of carbon monoxide.

Moreover, the two reactions have always been carried out separately and each in a discountinuous manner.

SUMMARY OF THE INVENTION

According to the present invention, on the other hand, a secondary amine and sulphur in stoichiometric proportions (1 mole of amine +0.5 mole of sulphur) are continuously fed together in a suitable solvent into a reaction column subjected to pressure by carbon monoxide and a continuous circulation of the reaction solution in the column is maintained, the said column forming part of an apparatus comprising further downstream an alkylation reaction vessel from which the desired substituted thiocarbamate is withdrawn continuously.

Furthermore, the said apparatus essentially comprises, in addition to the said reaction column—which is preferably a column filled with Raschig rings—and the said alkylation reaction vessel, a circulating pump for the liquid reactants and control means for the temperature.

The reacted solution is withdrawn from the alkylation reaction vessel in an amount equal (by weight) to that of the supplied reactants.

If it is desired to carry out the continuous process according to the invention with amine and sulphur in stoichiometric proportion to each other, it is essential that the sulphur be completely dissolved in the reaction mass which is introduced into the reaction column; in fact, proceeding differently and supplying a slurry must be excluded because of the technological difficulties which would arise in this case in the feed and in achieving the condition of stoichiometric proportions.

According to the invention, the dissolution of the sulphur is effected either by the amine itself, for example as in the event of hexamethyleneimine being employed, or by means of the addition of a certain amount of solution already reacted in the column, when the amine does not succeed in dissolving sulphur in the amount specified by the stoichiometry of the reaction, for example as when di-N-propylamine or ethylcyclohexylamine is used.

In the second case, use is made of the property of the solution of the thiocarbamic acid salt, obtained by the first reaction of the process, of dissolving the sulphur. That is, it is provided that the product which is formed be utilized for solubilizing the sulphur, that is one of the substances to be reacted. This obviously considerably extends the number of types of amines which can be used for conducting the said process efficiently.

The carbon monoxide is restored within the column as it is consumed. The amount of carbon monoxide in circulation is very small because of the smallness of the free volume in the reaction column. In consequence of this, in addition to the process and apparatus according to the invention having the normal advantages of a continuous process (high potentiality, small use of labour, etc.), they have an extreme degree of safety.

BRIEF DESCRIPTION OF THE DRAWING

The invention will now be described in greater detail with reference to the accompanying drawing, which illustrates diagrammatically an embodiment of the apparatus according to the invention, and with the aid of the examples that follow.

DESCRIPTION OF THE PREFERRED EMBODIMENT

The apparatus shown in the drawing provided two mixing reservoirs SA1 and SA2 which are connected alternately by means of a pump P1 to a conduit CO leading to the top of a reaction column C filled with Raschig rings RA. A reservoir B1 containing carbon monoxide under pressure is also connected to this column.

The reaction column C has at the bottom a collecting tank SC from the bottom of which there emerges a delivery conduit CE which bifurcates, being connected on one side to the conduit CO upstream of a circulating pump P2 and on the other side to a heat exchanger F1.

The top of the column C has a gas conduit CG leading to venting means SR2, SR3. The conduit CO is equipped in large part with a heating jacket R.

The exchanger F1 (the purpose of which is to cool the solution issuing from the collecting tank SC in order to avoid decomposition of the product during transition to ambient pressure) is connected to an alkylation reaction vessel SA3 equipped with a stirrer and an overflow TP from which a pipe TS leads to a storage tank SR1.

EXAMPLE 1

S-ethyl-N,N-hexamethylene thiocarbamate is prepared by the following reactions:

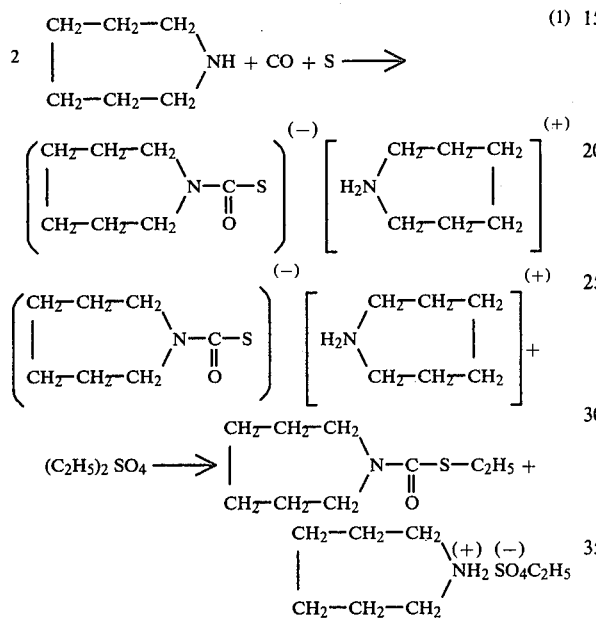

The reactants are introduced into a mixing reservoir, SA1 or SA2 alternately, with a capacity of 10 liters, in the following proportions:

Hexamethyleneimine 99%: 1000 g (10 moles)
Sulphur 160 g (5 moles)

Vigorous stirring is carried out until complete solubilization of the sulphur is obtained and then there is introduced:
Anhydrous toluene: 2600 g Stirring is maintained throughout the time of the feed.

Into the reaction column C, having a diameter of 5 cm and a height of 400 cm and being filled with Raschig rings and maintained at a temperature of 95°-105° C. by heating with a jacket and under a carbon monoxide pressure of 8-10 atm., there is delivered by means of the pump P1 the amount of mixture required to fill the collecting tank SC up to the level LI. The pump P2 is turned on so as to create a circulation in the column: the delivery of the pump is adjusted at a value between 60 and 200 l/h.

The mixture is left to circulate at a temperature of 95°-105° C. for 30-60 minutes and then the feed of the column by means of the pump P1 is resumed at a rate of 15-20 kg of mixture per hour.

A the same time, there is tapped off from the collecting tank SC an amount of reacted product equal to the fed amount, maintaining the level LI constant.

The carbon monoxide is supplied at the top and bottom of the column and is consumed in a practically theoretical amount; however, to avoid a concentration of gaseous impurities in the column, a certain amount of gas (1 or 2 bubbles per second) is eliminated through the venting means SR2 and SR3. The temperature in the column C is preferably maintained at 95°-105° C., making use of heating applied in a jacket R to the circulation conduit CO, inasmuch as at the lower temperatures the reaction is slower, while at higher temperatures it is possible to have decomposition of the product obtained.

The pressure in the column is preferably maintained at 8-10 atm., which is sufficient for good progress of the reaction. The quantity of product tapped off is cooled to 30°-40° C. in the exchanger F1 (it is necessary not to go below this temperature so as not to produce crystallization of the salt) and is delivered to the 10-liter ethylation reaction vessel SA3.

Simultaneously, diethyl sulphate is fed into the reaction vessel SA3 (3.1÷4.1 kg/h.).

The temperature in the ethylation reaction vessel SA3 is maintained at 35°-40° C. Fitted in the reaction vessel is a lateral outlet (calculated so as to achieve a permanence time of about 30 minutes in the reaction vessel) from which the reacted mass issues by overflowing and is sent to the storage tank SR1. By this process there is obtained a toluene solution of S-ethyl-N,N-hexamethylene thiocarbamate at about 23%. The total yield is higher than 90% of the theoretical.

EXAMPLE 2

S-ethyl dipropylthiocarbamate is prepared by the following reactions:

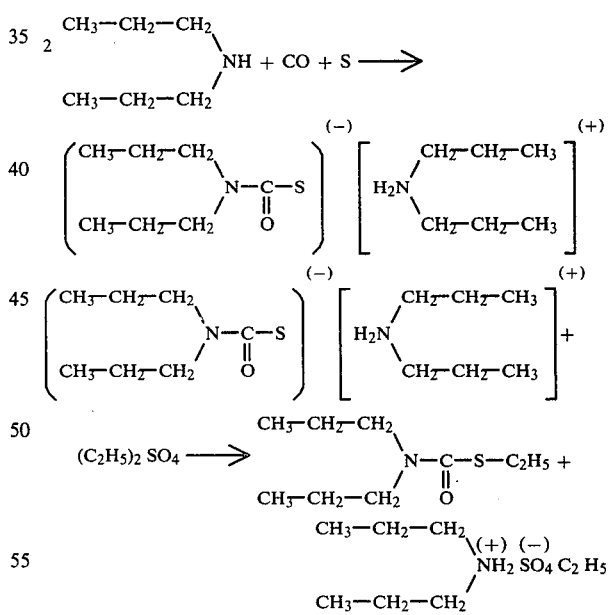

The same apparatus as is described in Example 1 is used.

The reactants are introduced into a mixing reservoir, SA1 or SA2 alternately, with a capacity of 10 liters, in the following proportions:

solution of the dipropylammonium salt of dipropylthiocarbamic acid at about 23% (in toluene): 3000 ml
di-N-propylamine at 98%: 678 ml
sulphur: 84 g Stirring is carried out until complete solubilization of the sulphur is obtained (it should be noted that the sulphur cannot dissolve in the di-N-propylamine alone, for which reason it is necessary to recycle the thiocarbamic acid salt) and then there is introduced Toluene: 1500 ml.

The amount of solution of the thiocarbamic acid salt introduced is not critical and is adjusted so as to obtain complete solubilization of the sulphur.

The operating conditions are as follows:
Column temperature: 80°–85° C.
Tapping-off temperature: 35°–40° C.
CO pressure in column: 8–10 atm.

$$2\ CH_2 \begin{array}{c} CH_2-CH_2 \\ \diagdown \\ \diagup \\ CH_2-CH_2 \end{array} HC-NH + CO + S \longrightarrow$$
$$\underset{CH_2-CH_3}{|}$$

$$\left[ CH_2 \begin{array}{c} CH_2-CH_2 \\ \diagdown \\ \diagup \\ CH_2-CH_2 \end{array} HC-N-\overset{O}{\underset{\|}{C}}-S \right]^{(-)} \left[ H_2N-CH \begin{array}{c} CH_2-CH_2 \\ \diagdown \\ \diagup \\ CH_2-CH_3 \end{array} \begin{array}{c} \diagdown \\ \diagup \\ CH_2-CH_2 \end{array} CH_2 \right]^{(+)}$$

Delivery of recycling pump (P2): 80–200 l/h.
Delivery of metering pump (P1): about 13 l/h.

The ethylation of the solution containing the salt obtained in the column C is carried out, as in Example 1, in the reaction vessel or tank SA3, supplying diethyl sulphate at a rate of about 860 ml/h. By this process there is obtained a toluene solution of S-ethyl dipropylthiocarbamate at about 23%. The total yield is higher than 85% of the theoretical. The yield can be increased to values higher than 95% if at the bottom of the reaction column there is connected a second, finishing, column similar to the first.

NOTE

Preparation of S-propyl dipropylthiocarbamate is possible by this second method by the following reaction:

The alkylating agent is different: propyl iodide is fed into the alkylation reaction vessel.

The yield is higher than 85%.

EXAMPLE 3

S-ethyl cyclohexylethylthiocarbamate is prepared by the following reactions:

The same apparatus as is described in Example 1 is used.

The reactants are introduced into a mixing reservoir, SA1 or SA2 alternately, with a capacity of 10 liters, in the following proportions:

Solution of the ethylcyclohexylammonium salt of ethylcyclohexylthiocarbamic acid at about 23%: 2000 g Ethylcyclohexylamine 97%: 640 g Sulphur: 80 g Vigorous stirring is carried out until complete solubilization of the sulphur in the salt and the amine is obtained and then there is added Anhydrous toluene: 1500 ml The operating conditions are as follows:
Temperature of column (C): 80°–100° C.
Tapping-off temperature 30°–40° C.
CO pressure in column: 8°–10 atm.
Delivery of recycling pump (P2): 80–200 l/h.
Delivery of metering pump (P1): 10–15 l/h.

The ethylation of the salt obtained in the column is carried out in a continuous manner as in Example 1 and 2, supplying diethyl sulphate at a rate of 760–1140 ml/h. By this process there is obtained a toluene solution of S-ethyl cyclohexylethylthiocarbamate at about 23%.

The total yield is higher than 85%.

To increase the yield, it is necessary, as in Example 2, to connect at the bottom of the column a second, finishing, column similar to the first.

I claim:

1. A continuous process for producing substituted thiocarbamates, comprising dissolving in stoichiometric proportions sulfur in a liquid selected from the group consisting of a secondary amine and a mixture of said amine and corresponding thiocarbamic acid salt, mixing the solution formed therefrom with a suitable solvent, continuously feeding said resultant mixture into a reaction column subjected to pressure by carbon monoxide, continuously circulating the resultant mixture in the column, continuously subjecting the effluent to alkylation, and continuously deriving the newly formed substituted carbamate therefrom.

2. Process as in claim 1, wherein the sulphur is completely dissolved in the amine and both are fed into the reaction column together with the solvent.

3. Process as in claim 1, wherein the sulphur is dissolved by a mixture of the amine and the solution of the thiocarbamic acid salt flowing from the column and recycled.

4. Apparatus for producing substituted thiocarbamates comprising a pair of mixing reservoirs, a reaction column filled with Raschig rings, a collecting tank at the bottom of the reaction column, a conduit for externally connecting the collecting tank to the top of the column, a circulating pump being connected in the said conduit and the said conduit being fed by the said mixing reservoirs by means of a second pump, and a pipe which branches from the said conduit to connect the bottom of the collecting tank to an alkylation reaction vessel via a heat exchanger, the alkylation reaction vessel comprising a stirrer and an overflow, the latter being connected to a storage tank.

5. Apparatus as in claim 4, wherein the said external circulation conduit is provided with a heating jacket over at least part of its length.

* * * * *